United States Patent
Mukherjee (12)

(10) Patent No.: US 9,248,262 B2
(45) Date of Patent: Feb. 2, 2016

(54) VASCULAR DILATOR FOR CONTROLLING BLOOD FLOW IN A BLOOD VESSEL

(75) Inventor: Dipankar Mukherjee, Vienna, VA (US)

(73) Assignee: Vibha Agarwal, Burke, VA (US)

( * ) Notice: Subject to any disclaimer, the term of this patent is extended or adjusted under 35 U.S.C. 154(b) by 674 days.

(21) Appl. No.: 12/923,043

(22) Filed: Aug. 31, 2010

(65) Prior Publication Data

US 2012/0053614 A1    Mar. 1, 2012

(51) Int. Cl.

| | |
|---|---|
| *A61M 29/00* | (2006.01) |
| *A61M 25/10* | (2013.01) |
| *A61B 17/12* | (2006.01) |
| *A61M 29/02* | (2006.01) |
| *A61B 17/22* | (2006.01) |
| *A61B 19/00* | (2006.01) |
| *A61M 25/00* | (2006.01) |
| *A61M 25/06* | (2006.01) |

(52) U.S. Cl.
CPC ...... *A61M 25/1011* (2013.01); *A61B 17/12045* (2013.01); *A61B 17/12109* (2013.01); *A61M 29/02* (2013.01); *A61B 2017/22038* (2013.01); *A61B 2019/462* (2013.01); *A61B 2019/4857* (2013.01); *A61M 25/0026* (2013.01); *A61M 25/0662* (2013.01); *A61M 2025/0008* (2013.01); *A61M 2025/1052* (2013.01)

(58) Field of Classification Search
CPC .......... A61B 17/12022; A61B 17/12145; A61B 2017/1205; A61B 17/1215; A61B 2017/00557; A61B 17/0218; A61B 17/12099; A61B 17/12136; A61B 17/12109; A61B 17/24; A61B 17/12104; A61M 29/00; A61M 29/02; A61M 25/10; A61M 25/1002; A61M 25/104; A61M 2025/0183; A61M 2025/1093; A61M 2025/1054; A61M 2210/0618; A61F 2/958; A61F 5/0093; A61F 7/12; A61F 2/07; A61F 2/88; A61F 5/08; A61F 2/95; A61H 21/00
USPC .......... 606/194, 159, 200, 190–192; 604/101.01–101.05
See application file for complete search history.

(56) References Cited

U.S. PATENT DOCUMENTS

| | | | | |
|---|---|---|---|---|
| 3,833,003 | A | * 9/1974 | Taricco | A61B 17/12045 604/103.11 |
| 4,404,971 | A | * 9/1983 | LeVeen | A61B 17/1204 604/101.05 |
| 4,540,404 | A | 9/1985 | Wolvek | |
| 4,576,142 | A | * 3/1986 | Schiff | A61M 1/1072 600/18 |
| 4,577,631 | A | * 3/1986 | Kreamer | A61B 17/12022 604/907 |
| 4,763,653 | A | * 8/1988 | Rockey | A61B 17/12 604/103.07 |
| 4,781,677 | A | * 11/1988 | Wilcox | A61B 17/22 600/561 |
| 4,909,798 | A | 3/1990 | Fleischhacker et al. | |

(Continued)

OTHER PUBLICATIONS

Michelle Followell, http://www.avainfo.org/website/download.asp?id=162735; Mar. 2010.*

(Continued)

*Primary Examiner* — Amy R Weisberg
(74) *Attorney, Agent, or Firm* — Dinesh Agarwal, P.C.

(57) ABSTRACT

A vascular dilator for controlling blood flow in a blood vessel, includes an elongate body for inserting into a blood vessel and a generally tapered distal end portion and a proximal end portion, and a plurality of inflatable members positioned adjacent the distal end portion. The inflatable members are longitudinally spaced from one another by a predetermined distance.

20 Claims, 8 Drawing Sheets

(56) References Cited

U.S. PATENT DOCUMENTS

| | | | |
|---|---|---|---|
| 5,092,857 A | 3/1992 | Fleischhacker | |
| 5,246,421 A * | 9/1993 | Saab | 606/194 |
| 5,458,574 A * | 10/1995 | Machold | A61M 25/1011 604/101.03 |
| 5,496,271 A * | 3/1996 | Burton | A61B 18/18 604/101.05 |
| 5,542,936 A * | 8/1996 | Razi | A61M 25/0043 604/158 |
| 5,669,881 A * | 9/1997 | Dunshee | A61M 25/065 604/164.1 |
| 5,830,125 A | 11/1998 | Scribner et al. | |
| 5,919,163 A * | 7/1999 | Glickman | A61M 25/1011 604/101.05 |
| 6,165,196 A * | 12/2000 | Stack | A61B 17/11 606/194 |
| 6,537,247 B2 | 3/2003 | Shannon | |
| 6,569,190 B2 * | 5/2003 | Whalen et al. | 623/1.1 |
| 6,719,724 B1 * | 4/2004 | Walker | A61F 7/123 604/101.01 |
| 6,733,474 B2 | 5/2004 | Kusleika | |
| 7,169,171 B2 * | 1/2007 | Don Michael | A61F 2/013 623/1.11 |
| 7,335,192 B2 * | 2/2008 | Keren | A61M 1/101 604/101.03 |
| 7,819,841 B2 * | 10/2010 | Horrigan | A61B 17/12036 604/104 |
| 7,914,577 B2 * | 3/2011 | Cox | A61F 2/2451 623/2.37 |
| 2001/0021849 A1 * | 9/2001 | Swartz | A61B 18/1492 606/41 |
| 2002/0183777 A1 | 12/2002 | Shannon | |
| 2003/0109915 A1 * | 6/2003 | Don Michael | A61F 2/013 623/1.11 |
| 2004/0093044 A1 * | 5/2004 | Rychnovsky | A61B 18/245 607/88 |
| 2005/0027247 A1 * | 2/2005 | Carrison | A61M 25/1011 604/101.01 |
| 2005/0038502 A1 * | 2/2005 | Waysbeyn | A61B 17/3478 623/1.23 |
| 2005/0055043 A1 * | 3/2005 | Foltz | A61M 25/1011 606/193 |
| 2005/0283181 A1 * | 12/2005 | Ravikumar | A61M 25/1011 606/194 |
| 2007/0021770 A1 * | 1/2007 | Brenneman | A61B 17/0057 606/192 |
| 2007/0135793 A1 * | 6/2007 | Barbut | A61B 5/0215 604/509 |
| 2008/0065011 A1 | 3/2008 | Marchand et al. | |
| 2008/0132937 A1 * | 6/2008 | Hartley | A61B 17/12045 606/194 |
| 2008/0200946 A1 * | 8/2008 | Braun | A61M 25/0054 606/198 |
| 2008/0275391 A1 * | 11/2008 | Lyons | A61M 16/0472 604/96.01 |
| 2009/0054922 A1 * | 2/2009 | Broker | A61M 25/1002 606/194 |
| 2009/0281564 A1 * | 11/2009 | Kontos | A61M 25/104 606/194 |
| 2010/0022948 A1 | 1/2010 | Wilson et al. | |
| 2010/0076484 A1 * | 3/2010 | Riina | A61F 2/958 606/213 |
| 2010/0121345 A1 * | 5/2010 | Brasington et al. | 606/127 |
| 2013/0102926 A1 * | 4/2013 | Eliason | A61M 25/04 600/585 |

OTHER PUBLICATIONS

Wikipedia, http://en.wikipedia.org/wiki/Seldinger_technique, Dec. 2005.*

Castelli et al "Emergency endovascular repair for traumatic injury of the inferior vena cava" European Journal of cardio thoracic surgery 2005 pp. 906-908.*

* cited by examiner

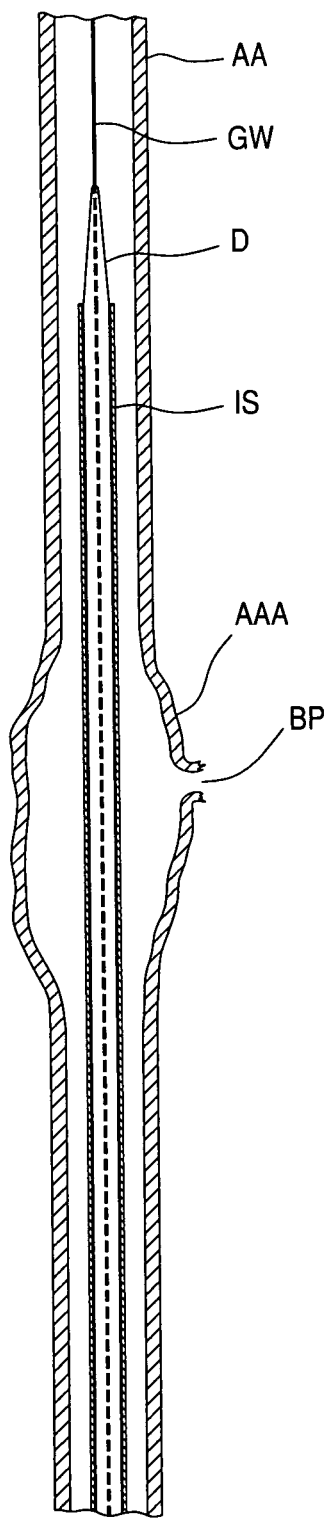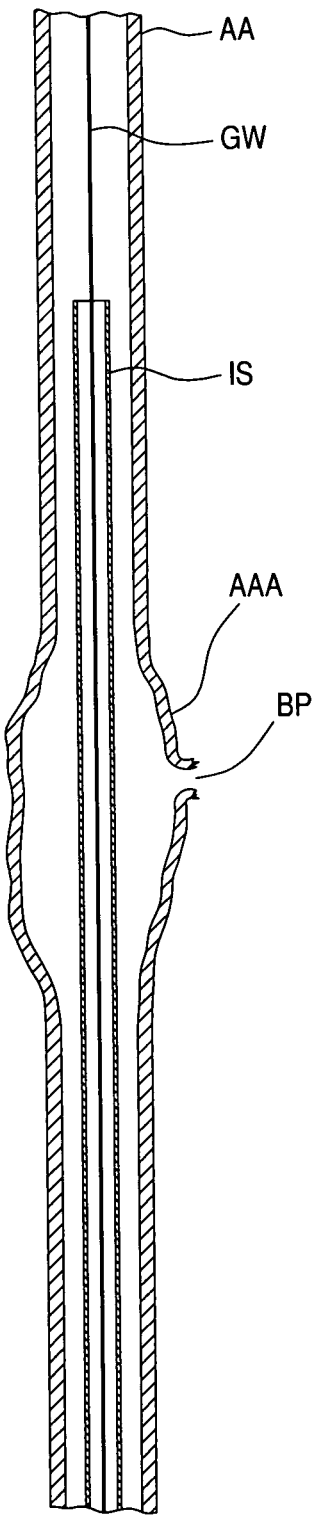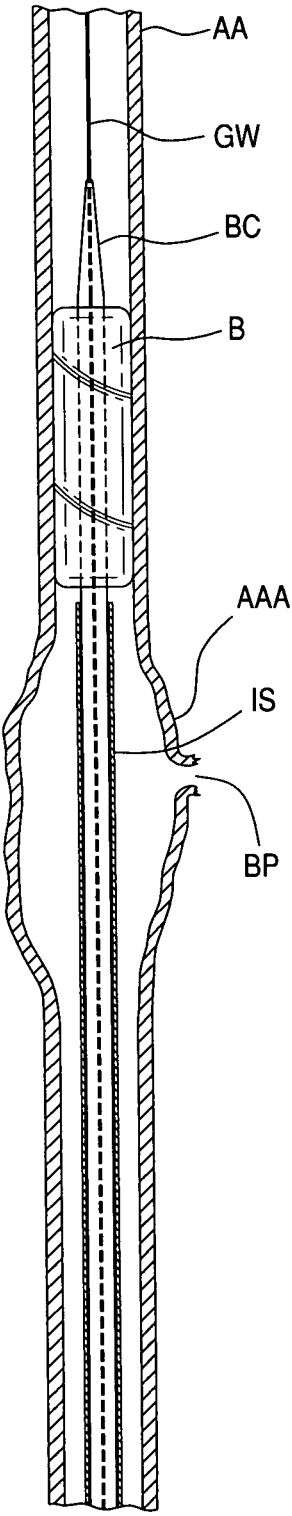
FIG. 5
PRIOR ART
FIG. 6
PRIOR ART
FIG. 7
PRIOR ART

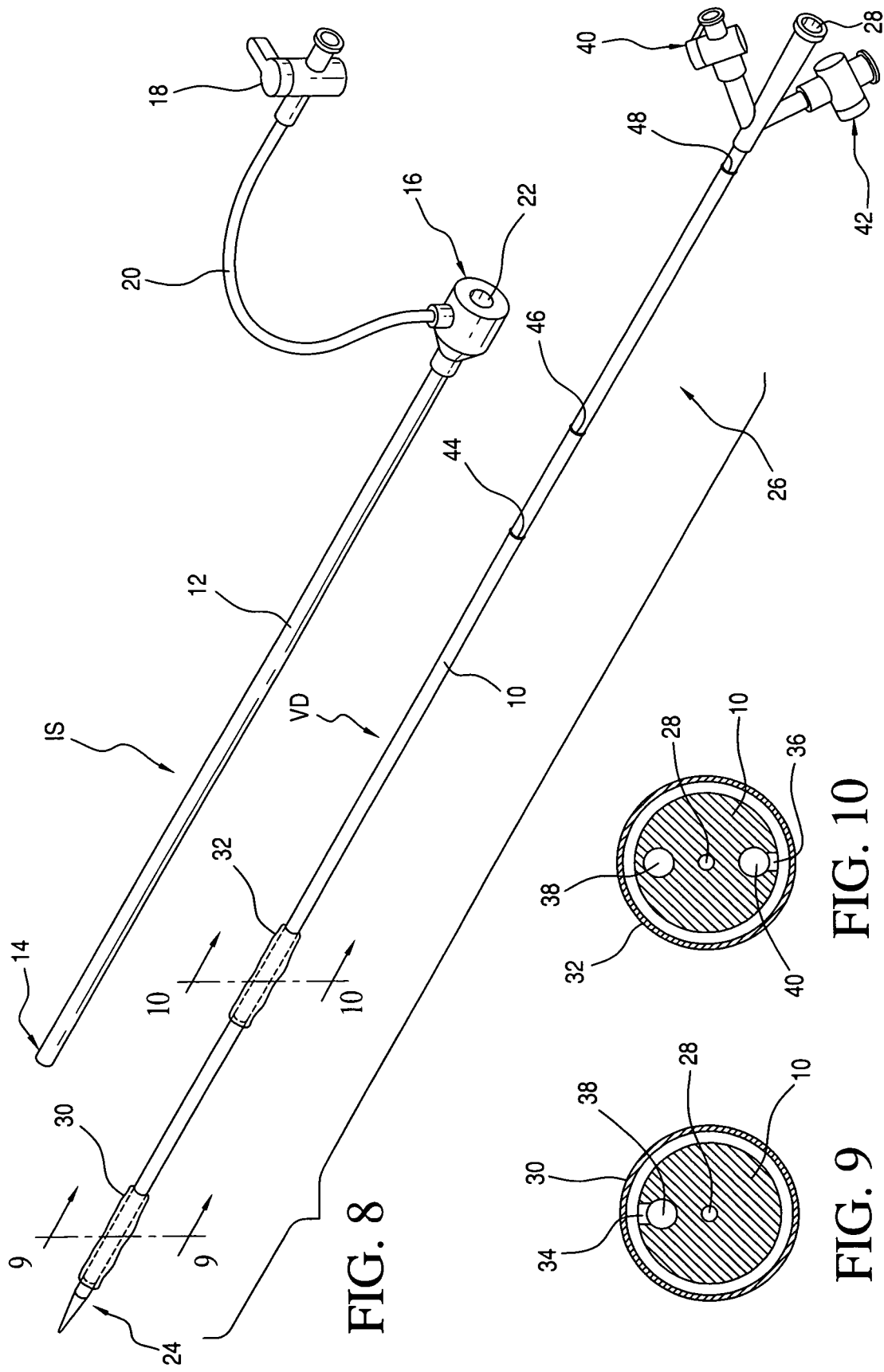

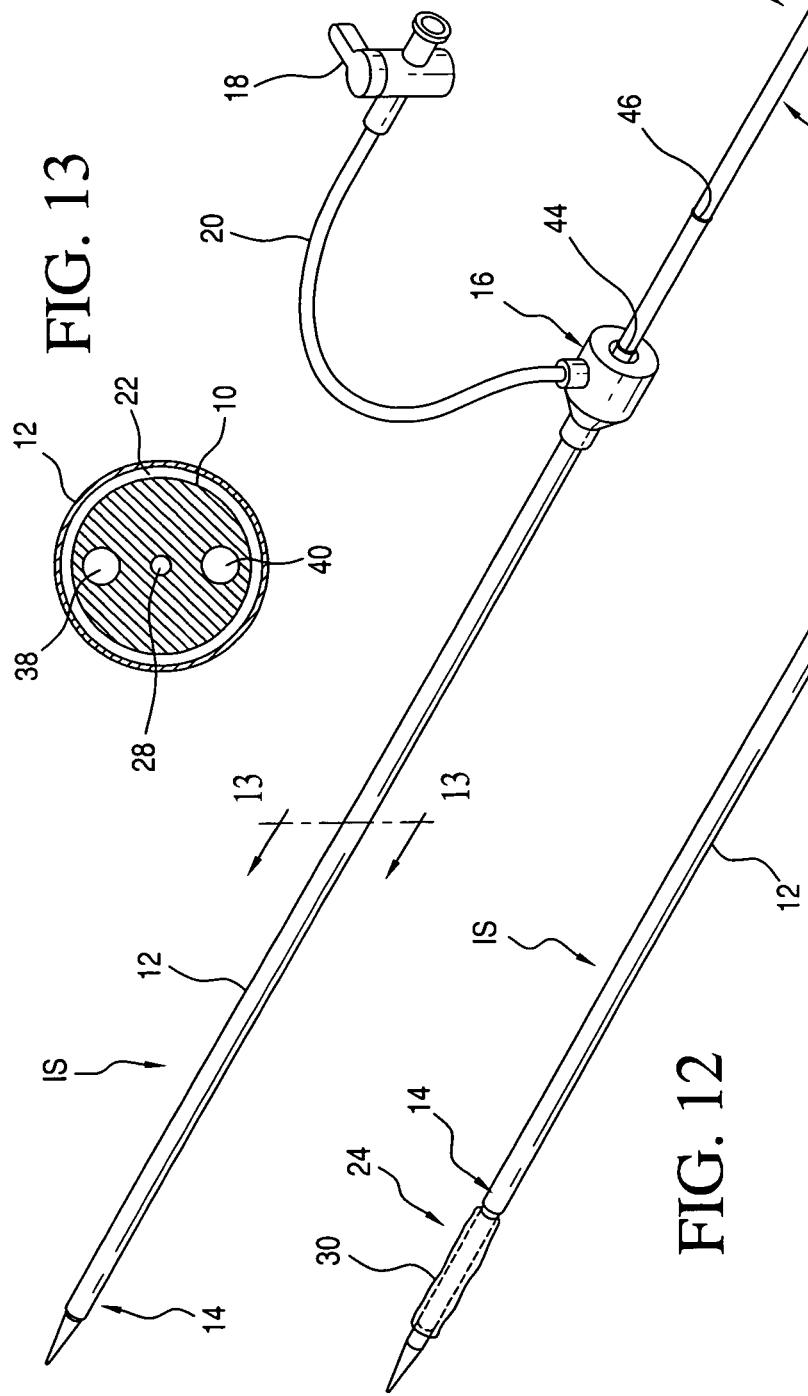

VASCULAR DILATOR FOR CONTROLLING BLOOD FLOW IN A BLOOD VESSEL

FIELD AND BACKGROUND OF THE INVENTION

The present invention is generally directed to surgical instruments and procedures, and more particularly to a vascular dilator for controlling blood flow in a blood vessel.

Massive bleeding from an arterial or venous blood vessel is one of the major causes of death in acute trauma. In addition, massive bleeding from ruptured aneurysm of an abdominal aorta or thoracic aorta is the usual mode of death for these patients. It is estimated that about 80% of ruptured aneurysm occurs in an abdominal aorta (FIG. 3) and about 20% in a thoracic aorta (FIG. 2). Iatrogenic cause of massive bleeding from perforation or rupture of a major blood vessel can also be a cause of mortality and morbidity from this incident.

Following rupture of an abdominal aortic aneurysm, the mortality from this condition has been traditionally at least 50% of those patients who reach the hospital and are taken to surgery or repair of the aneurysm. Recent advances in the management of ruptured abdominal aortic aneurysms, including balloon control of bleeding from the aorta and, when possible, endovascular repair of the abdominal aortic aneurysm, rather than open repair, has shown encouraging improvement in the mortality and morbidity of this condition. Recent reports have suggested mortality from ruptured abdominal aortic aneurysms in the order of 20-25%, compared with the previous 50%. Morbidity is also a fraction of what traditionally had been the case with open repair.

Emerging surgical literature would suggest that early balloon control of the aorta in a patient with massive bleeding from a ruptured abdominal aortic aneurysm, results in marked improvement in survival, even in those patients who ultimately undergo open surgical repair of the aneurysm because the anatomy of the aneurysm did not lend itself to endovascular repair.

Referring to FIGS. 1-7, conventionally, when a patient (P) with, for example, a ruptured abdominal aortic aneurysm (AAA) arrives at the emergency room of an hospital, he/she undergoes an expeditious CT scan to prove the condition. Once proven, the patient is whisked to the operating room and, under the current approach of early balloon control of the aorta, the femoral artery (FA) in the groin is punctured under ultrasound guidance and a guidewire (GW) is advanced under fluoroscopic guidance into the abdominal aorta (AA) above the source of bleeding or bleeding point (BP). A large introducer sheath (IS) and a dilator (D) complex is then advanced over the wire into the aorta (AA). (This dilator and sheath complex is typically long enough to allow a balloon (B) of a catheter to occlude the aorta above the source of bleeding.) Traditionally, when the patient has a ruptured abdominal aortic aneurysm, a 12-French sheath (IS) 45 cm long with an inner dilator (D) in place, is advanced over the guidewire (GW) (FIG. 5). The dilator (D) is next removed, leaving the guidewire and sheath in place (FIG. 6). A large balloon catheter (BC) is then fed over the guidewire (GW), through the sheath (IS), and then inflated in the aorta above the source of bleeding (FIG. 7). The 45 cm long sheath helps hold the balloon (B) in place to prevent it from being pushed down with each beat of the heart.

Once the aorta is controlled, the patient is fully resuscitated with blood and blood products until normal hemodynamic parameters are obtained. Repair of the aorta can now proceed as appropriate based on the anatomy of the pathologic process. If endovascular repair is possible, this is ideal. If endovascular repair is not possible, then open repair can be performed. Once the abdomen is opened, the aorta is controlled in a standard fashion. Once a clamp is placed on the aorta, the balloon is removed along with the sheath. Open repair of the abdominal aortic aneurysm can then be performed in standard manner.

The above technique/procedure can be applied to any major blood vessel in the body that is injured or ruptured for a variety of reasons. This is particularly relevant in cases of massive venous bleeding, such as a tear of the vena cava, which can occur in acute traumatic situations, and is frequently the cause of death in such individuals. Massive pelvic injury and many abdominal injuries lead to demise of the patient on account of massive venous bleeding. The same technique/procedure of balloon control of the vena cava, or a major vein, both above and below the site of injury, would be lifesaving.

Various catheters, dilators, and introducer sheaths are currently available as shown in U.S. Pat. Nos. 4,540,404; 4,909,798; 5,092,857; 5,669,881; 5,830,125; 6,537,247; 6,733,474; 2002/0183777; 2008/0065011; and 2010/0022948.

ASPECTS OF THE INVENTION

The present disclosure is directed to various aspects of the present invention.

One aspect of the present invention includes a vascular dilator for controlling blood flow in a blood vessel.

Another aspect of the present invention includes a vascular dilator for controlling bleeding from a blood vessel.

Another aspect of the present invention includes a vascular dilator which eliminates the need for using a balloon catheter in controlling bleeding or blood flow in a blood vessel.

Another aspect of the present invention includes a vascular dilator for management and/or control of an aneurysm, such as an abdominal or thoracic aneurysm.

Another aspect of the present invention includes a vascular dilator for management and/or control of an abdominal or thoracic aneurysm, particularly in a ruptured state.

Another aspect of the present invention includes a vascular dilator for management and/or control of an aneurysm or bleeding from a blood vessel to reduce mortality and morbidity.

Another aspect of the present invention includes a vascular dilator for controlling blood flow or bleeding in a blood vessel that reduces the overall time needed to repair a blood vessel or an aneurysm.

Another aspect of the present invention includes a vascular dilator which can control antegrade, as well as retrograde flow of blood in a blood vessel.

Another aspect of the present invention includes a method, technique, or medical procedure, which reduces the time needed to control blood flow or bleeding in a blood vessel of a subject.

Another aspect of the present invention includes a method, technique, or medical procedure, which reduces the overall time needed to repair a blood vessel or an aneurysm of a subject.

Another aspect of the present invention includes a method, technique, or medical procedure, which can control antegrade, as well as retrograde flow of blood in a blood vessel.

Another aspect of the present invention includes a vascular dilator for controlling blood flow in a blood vessel, including an elongate body for inserting into a blood vessel and including a generally tapered distal end portion and a proximal end portion, and a plurality of inflatable members positioned adjacent the distal end portion. The inflatable members are longitudinally spaced from one another by a predetermined distance.

Another aspect of the present invention includes a vascular apparatus for controlling blood flow in a blood vessel, including an introducer sheath having a generally pliable tubular body and including an open distal end portion and a proximal end portion, and a dilator having a generally rigid body and including distal and proximal end portions. The dilator includes a plurality of longitudinally spaced inflatable members positioned adjacent the distal end portion thereof, and includes an external diameter less than an internal diameter of the introducer sheath to allow insertion therethrough to selectively position one of the inflatable members outside of and adjacent the open distal end portion of the introducer sheath.

Another aspect of the present invention includes a kit for use in controlling blood flow in a blood vessel, including an introducer sheath having a generally pliable tubular body and including an open distal end portion and a proximal end portion, and a dilator having a generally rigid body and including distal and proximal end portions. The dilator includes a plurality of longitudinally spaced inflatable members positioned adjacent the distal end portion thereof, and includes an external diameter less than an internal diameter of the introducer sheath to allow insertion therethrough.

Another aspect of the present invention includes a method of controlling blood flow in a blood vessel of a subject, including: providing a dilator including distal and proximal end portions, and a plurality of longitudinally spaced inflatable members positioned adjacent the distal end portion thereof; advancing the dilator through an introducer sheath including an open distal end portion, already in place in a blood vessel, such that a selected one of the inflatable members passes through the open distal end portion of the introducer sheath; and inflating the selected one inflatable member to block the flow of blood through the blood vessel.

Another aspect of the present invention includes a method of controlling bleeding from a blood vessel of a subject, including: providing a dilator including distal and proximal end portions, and a plurality of longitudinally spaced inflatable members positioned adjacent the distal end portion thereof; providing an introducer sheath including an open distal end portion and a proximal end portion; advancing the introducer sheath through a bleeding blood vessel until the open distal end portion thereof passes the bleeding point; advancing the dilator through the introducer sheath such that a selected one of the inflatable members passes through the open distal end portion of the introducer sheath; and inflating the selected one inflatable member to block an antegrade flow of blood adjacent the bleeding point.

Another aspect of the present invention includes a method of controlling bleeding from a blood vessel of a subject, including: providing a dilator including distal and proximal end portions, and a plurality of longitudinally spaced inflatable members positioned adjacent the distal end portion thereof; providing an introducer sheath including an open distal end portion and a proximal end portion; advancing the introducer sheath through a bleeding blood vessel until the open distal end portion thereof reaches near the bleeding point; advancing the dilator through the introducer sheath such that selected first and second of the inflatable members pass through the open distal end portion of the introducer sheath; and inflating the selected second inflatable member to block an antegrade flow of blood adjacent the bleeding point.

BRIEF DESCRIPTION OF THE DRAWINGS

One of the above and other aspects, novel features and advantages of the present invention will become apparent from the following detailed description of a preferred embodiment(s) of the invention, as illustrated in the drawings, in which:

FIG. 5 illustrates the prior art device of FIG. 4, on a guidewire extending through an abdominal aortic aneurysm;

FIG. 6 is a view similar to FIG. 5, showing the dilator removed and leaving the guidewire and introducer sheath in place;

FIG. 7 is a view similar to FIG. 6, showing a balloon catheter inserted through the introducer sheath and the balloon inflated above the source of bleeding;

FIG. 8 is an exploded perspective view of an embodiment of the device of the present invention;

FIG. 9 is an enlarged sectional view taken along line 9-9 of FIG. 8;

FIG. 10 is an enlarged sectional view taken along line 10-10 of FIG. 8;

FIG. 11 is a perspective view of an embodiment of the dilator of the present invention, shown inserted through the introducer sheath;

FIG. 12 is a partial view similar to FIG. 11, showing the introducer sheath retracted to the second marker to expose the first inflatable member;

FIG. 13 is an enlarged sectional view taken along line 13-13 of FIG. 11;

DETAILED DESCRIPTION OF THE PREFERRED EMBODIMENT(S) OF THE INVENTION

Figure 1:
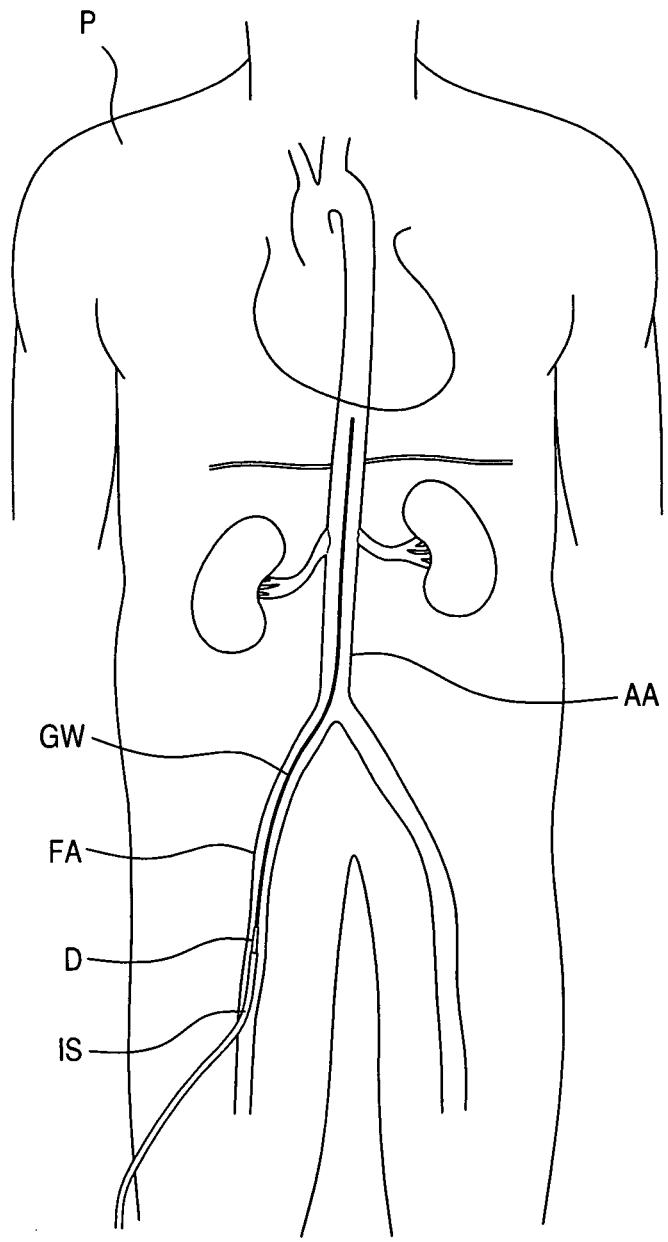
FIG. 1 is a front view of a human body with normal aorta, showing for illustration purposes a guidewire inserted into the right femoral artery and extending up into the aorta, and a sheath/dilator complex being inserted over the guidewire.
Figure 2:
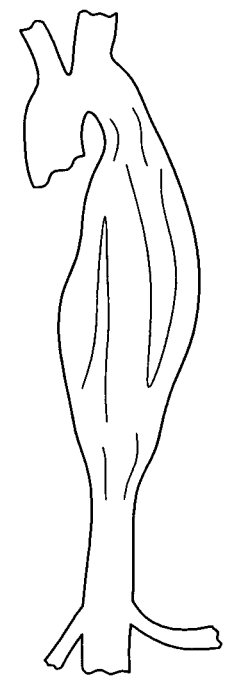
FIG. 2 illustrates a thoracic aortic aneurysm.
Figure 3:
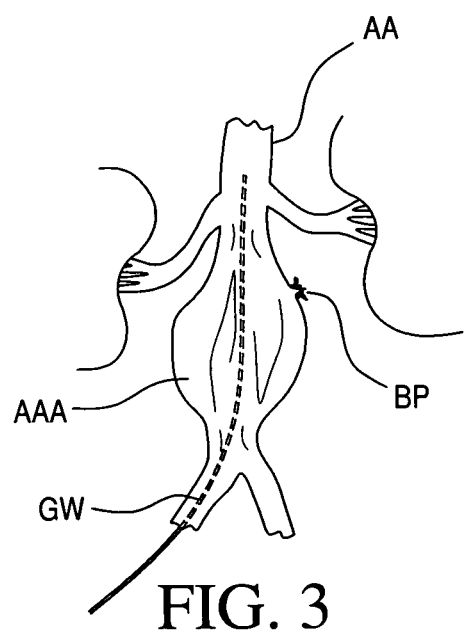
FIG. 3 illustrates an abdominal aortic aneurysm.
Figure 4:
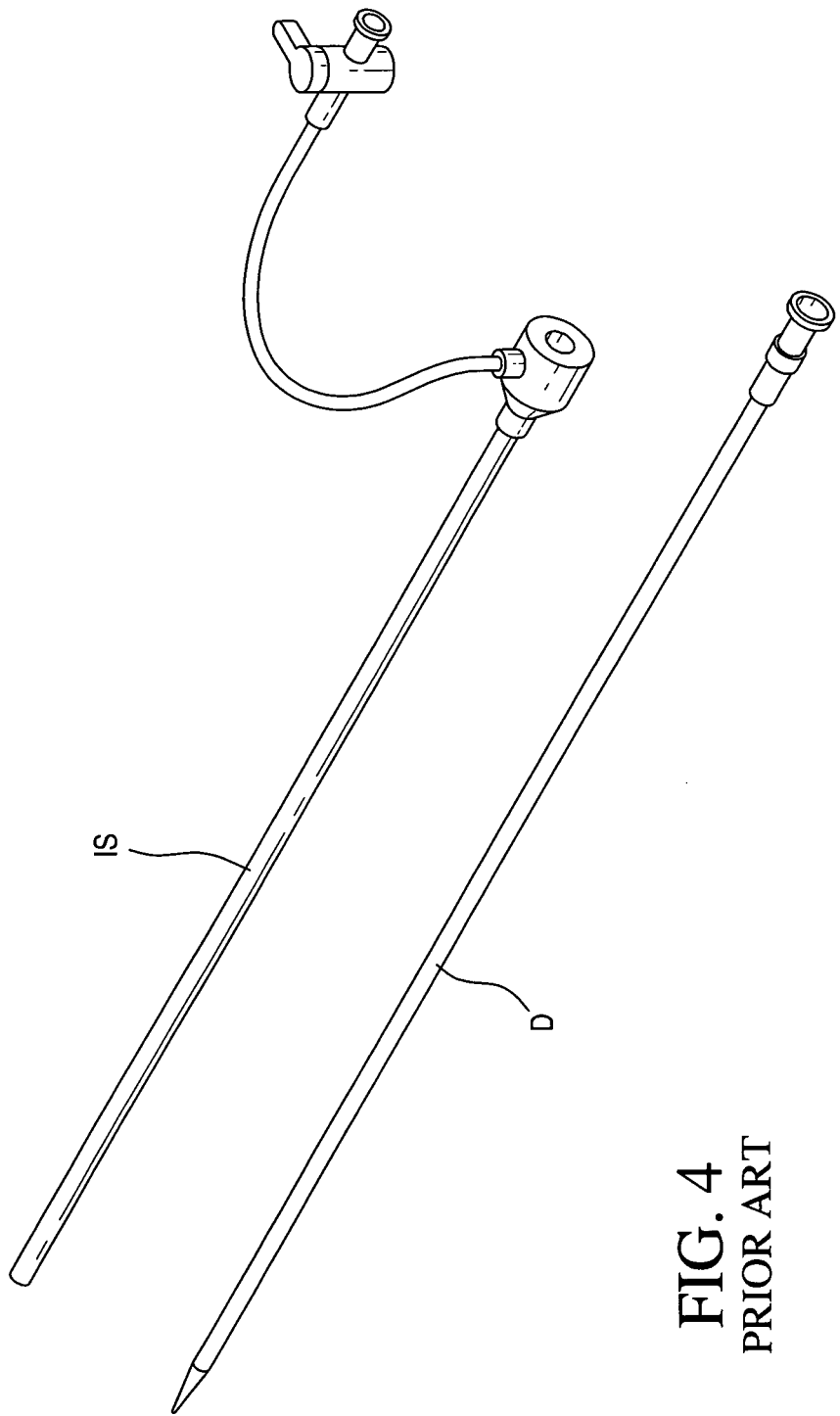
FIG. 4 is a perspective view of the prior art device including an introducer sheath and a dilator.

Referring to FIGS. 9-12, a vascular dilator VD, in accordance with a preferred embodiment of the present invention, includes an elongate body 10, preferably made of a rigid material and having an external diameter less than the internal diameter of the introducer sheath IS. Conventionally, the introducer sheath IS is made of a generally pliable tubular body 12, and includes an open distal end portion 14, and a proximal end portion 16 equipped with a stop cock 18 and an associated tubing 20 for introducing, for example, an irrigation fluid through a lumen 22 thereof.

The body 10 of the vascular dilator VD includes, a preferably-tapered distal end portion 24 and a proximal end portion 26. A preferably central lumen 28 extends through the length of the body 10 for allowing, for example, a guidewire GW to extend therethrough.

Adjacent the distal end portion 24 of the vascular dilator VD, are provided first and second inflatable members 30 and 32, which are longitudinally or axially spaced from each other by a predetermined distance. Preferably, the distance between the first and second inflatable members 30 and 32 ranges from about 2 to about 15 cm. The inflatable members 30 and 32 are preferably balloons, which can be inflated by introducing a fluid therein through corresponding ports 34 and 36 (FIGS. 9 and 10).

As best shown in FIGS. 9 and 10, the body 10 includes two peripherally oriented inflation lumens 38 and 40 that are in fluid communication with the ports 34 and 36, respectively. The inflation lumens 38 and 40 run axially along the length of the body 10 from the corresponding first and second inflatable members 30 and 32, towards the proximal end portion 26, where they are in fluid communication with the corresponding stop cock mechanisms 40 and 42, respectively. It is noted herewith that although the vascular dilator VD has been shown and described as having two inflatable members, it is within the scope of this invention to provide additional inflatable members.

As best shown in FIG. 8, the body 10 of the vascular dilator VD includes first, second, and third markers 44, 46 and 48, respectively, adjacent the proximal end portion 26 thereof. The markers 44, 46 and 48 can be in the form of color-coded bands, grooves, or ridges, to provide the surgeon or other medical professional a visual or tactile indicator of the positions of the first and second inflatable members 30 and 32, relative to the open distal end portion 14 of the introducer sheath IS. In other words, the positions and the number of the markers 44, 46 and 48 are selected so as to indicate the positions of the inflatable members 30 and 32 in a blood vessel, and more specifically relative to the distal end portion 14 of the introducer sheath IS.

As best illustrated in FIGS. 11-12, when the first marker 44 is generally aligned with the proximal end portion 16 of the introducer sheath, both the inflatable members 30 and 32 remain inside of the introducer sheath body 12 (FIG. 11). As the body 10 of the vascular dilator VD is pushed further into the introducer sheath IS (or the introducer sheath IS is withdrawn relative to the vascular dilator VD) such that the second marker 46 comes to align with the proximal end portion 16 of the introducer sheath IS, the first (or forward) inflatable member 30 projects out of the introducer sheath IS and is positioned at or adjacent the open distal end portion 14 (FIG. 12). In the same manner, as shown in FIG. 16, when the third marker 48 is in alignment with the proximal end portion 16 of the introducer sheath IS, both the first (forward) and second (rearward) inflatable members 30 and 32 are positioned externally of the introducer sheath IS, adjacent the open distal end portion 14 thereof.

Figure 14:
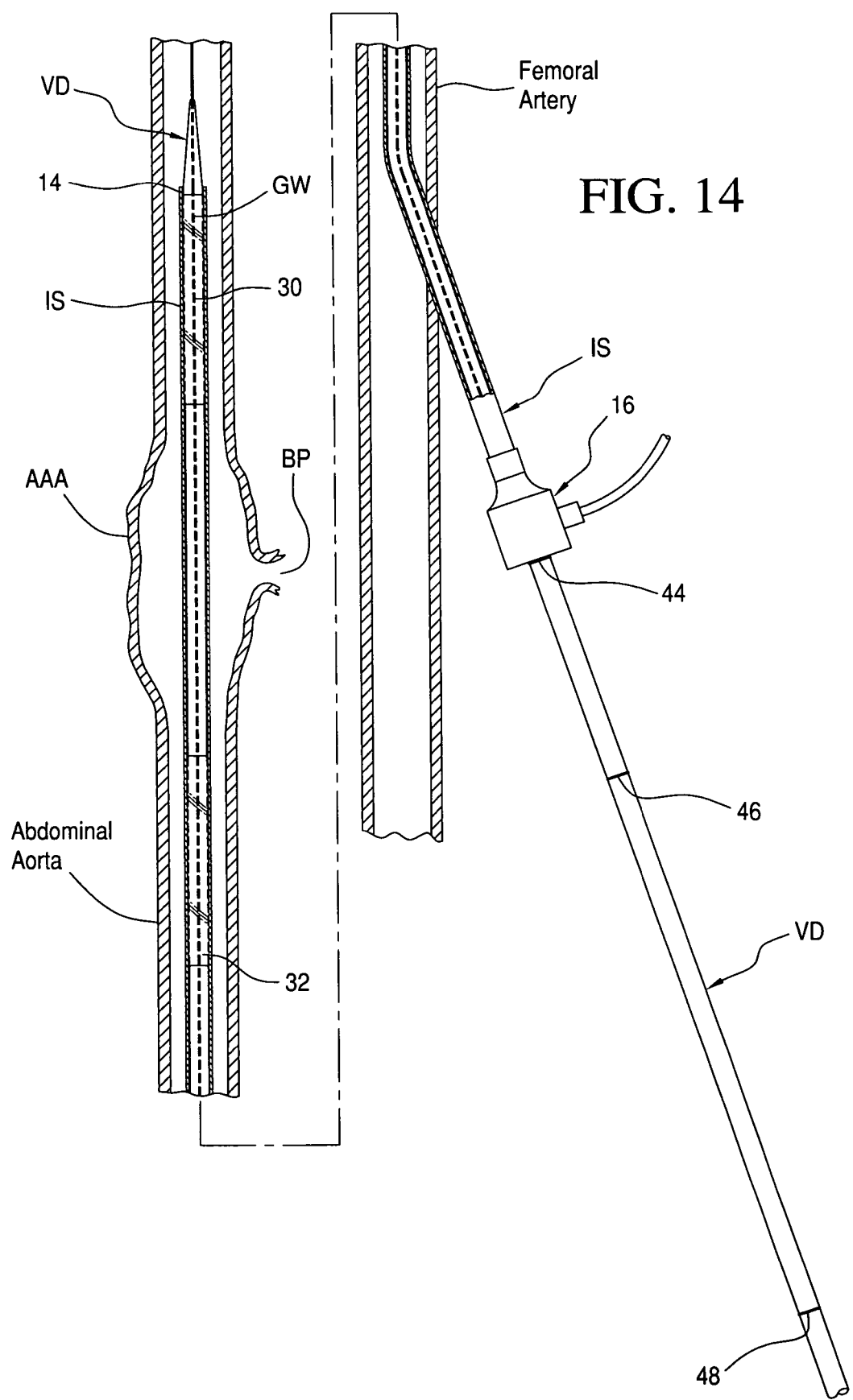
FIG. 14 is a view of the device of the present invention, shown inserted over the guidewire and extending past an aneurysm.
Figure 15:
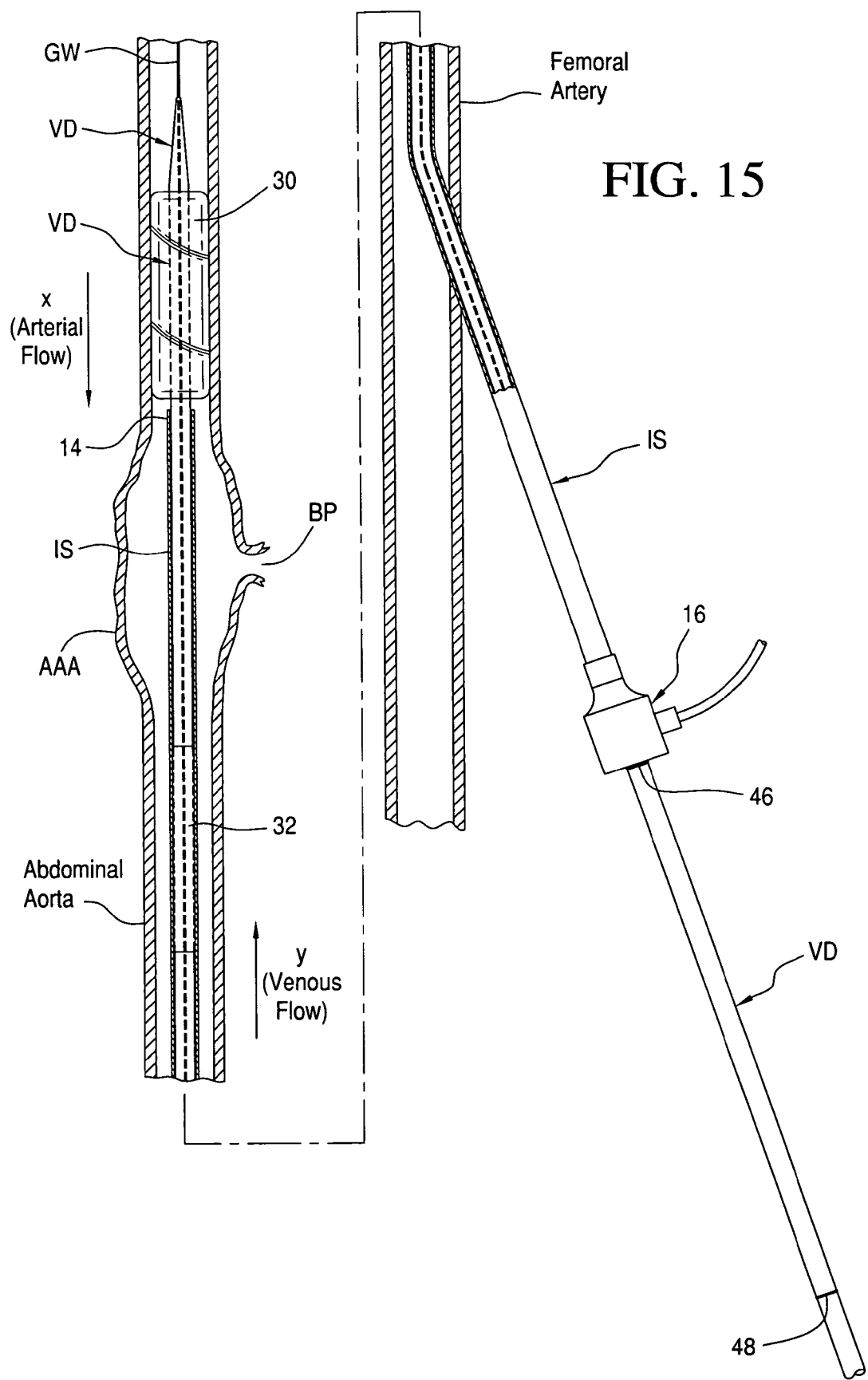
FIG. 15 is a view similar to FIG. 14, showing the introducer sheath retracted to the second marker to expose the first inflatable member, shown inflated.
Figure 16:
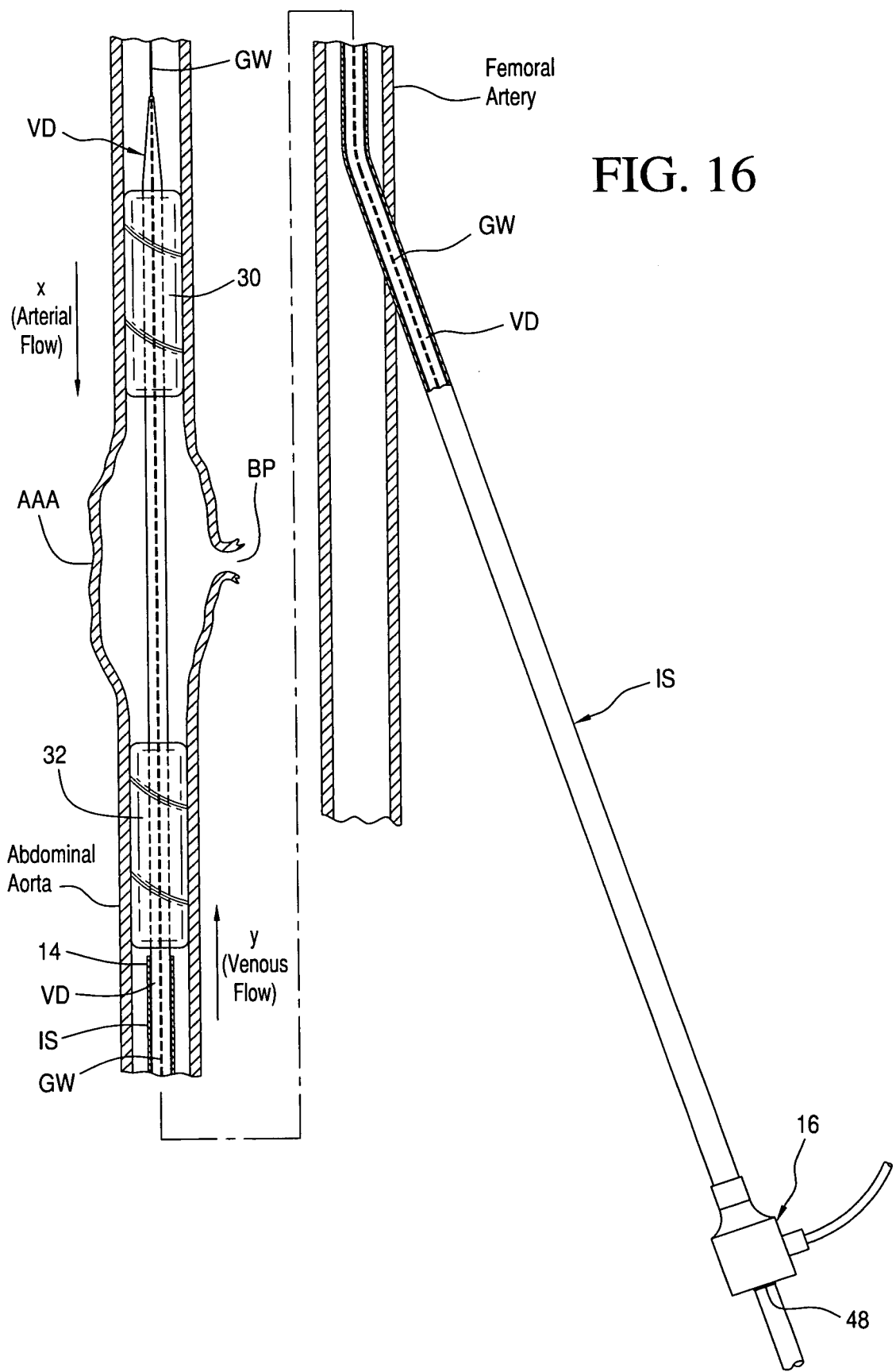
FIG. 16 is a view similar to FIG. 15, showing the introducer sheath retracted to the third marker to expose the second inflatable member, shown inflated.

Referring to FIGS. 14-16, a method, technique, or medical procedure for management and control of an abdominal aortic aneurysm AAA, by using the vascular dilator VD, in conjunction with an introducer sheath IS, will now be described.

As described above and as shown in FIG. 14, the introducer sheath IS and vascular dilator VD, are advanced over the guidewire GW through the abdominal aorta AA, in a known manner such that the open distal end portion 14 of the introducer sheath IS is positioned above or beyond the aneurysm AAA. The position of the first inflatable member 30 inside of and adjacent the open distal end portion 14 of the introducer sheath IS is confirmed by the first marker 44 being in general alignment with the proximal end portion 16 of the introducer sheath IS. (This position can also be confirmed by other conventional equipment and/or means, such as a CT scan, fluroscope, radioscope, and/or ultrasound guidance.) Once confirmed, or at the surgeon's experience and discretion, the introducer sheath IS is withdrawn relative to the vascular dilator VD, such that the second marker 46 is in alignment with the proximal end portion 16 of the introducer sheath IS (FIG. 15). In this position, the first inflatable member 30 would be out of the introducer sheath IS and positioned at or adjacent the open distal end portion 14 thereof. By actuating the associated stop cock mechanism 40, the surgeon then introduces an appropriate inflation fluid through the associated inflation lumen 38 and the port 34, into the inflatable member 30, such that the inflated member 30 comes to engage the internal wall of the abdominal aorta AA, thereby occluding the vessel. One of ordinary skill in the art would appreciate that since the blood would be flowing in a direction shown by arrow 'X,' the inflation of the first inflatable member 30, in this manner, would control or stop the antegrade flow of blood through the abdominal aorta AA, upstream of the abdominal aortic aneurysm AAA (or the bleeding point BP). One would further appreciate that if the blood vessel were a vein, the flow of blood would be in the opposite direction, as shown by arrow 'Y' in FIG. 15. Therefore, an antegrade flow of blood would also be controlled or stopped, however, it would be downstream of the aneurysm AAA or the bleeding point BP.

As illustrated in FIG. 16, once the first inflatable member 30 has been inflated to stop an antegrade flow of blood through the abdominal aorta AA, the introducer sheath IS is withdrawn further relative to the vascular dilator VD, such that the third marker 48 comes to align with the proximal end portion 16 of the introducer sheath IS (FIG. 16). This causes the second (or rearward) inflatable member 32 to be exposed out of the introducer sheath IS, and be positioned at or adjacent the open distal end portion 14 thereof. Now, by actuating the stop cock mechanism 42, the surgeon can inject an appropriate fluid into the second inflatable member 32, via the inflatable lumen 40 and the associated port 36. This would control or stop the retrograde bleeding or blood flow. One would also appreciate that the second inflatable member 32 controls or stops the blood flow downstream of the abdominal aortic aneurysm AAA or the bleeding point BP.

One would also appreciate that since the flow of blood in a vein is in the opposite direction (shown by a arrow 'Y' in FIGS. 15-16), the positioning and inflation of the second inflatable member 32, in the manner described above, would also control the antegrade blood flow, however, it would be upstream of the aneurysm AAA or the bleeding point BP.

It is noted herewith that in the case of an abdominal aortic aneurysm, only the first inflatable member 30 need to be inflated, since the bleeding from the aorta would have been controlled, and the repair usually involves an aortobiiliac repair or an aortouniiliac repair, with a plug placed in the contralateral common iliac artery to prevent retrograde bleeding followed by a femoral-to-femoral bypass graft to provide perfusion to the contralateral lower extremity.

It is further noted that it is within the scope of the invention to reverse or vary the order for inflating the inflatable members 30 and 32. For instance, in a procedure, both inflatable members 30 and 32 could be exposed or positioned out of the introducer sheath IS, and then any order for inflation thereof would be achieved, including simultaneously. It is also within the scope of the invention to provide more than two inflatable members with desired distance(s) between them.

It is also noted herewith that although the method described herein includes approaching an aneurysm or bleeding point from the lower side of the patient, i.e., the groin area, it is within the scope of the invention to make an approach from the upper side. For example, in a thoracic bleeding or aneurysm, the introducer sheath IS and vascular dilator could be advanced through an entry point in the chest area of the patient.

From the above, one would appreciate that the vascular dilator VD of the present invention, with the built-in balloons, can be expeditiously inflated to effectively control blood flow or bleeding, without having to first withdraw or remove a conventional dilator and then introduce a separate balloon catheter, both of which steps require additional time and maneuvering.

While this invention has been described as having preferred sequences, ranges, steps, materials, structures, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and/or the claims appended hereto.

What is claimed is:

1. A method of repairing an aneurysm in an arterial blood vessel of a subject, comprising the steps of:
    a) providing a dilator-introducer sheath complex, consisting of:
        i) a dilator, consisting of:
            an elongate generally rigid body having a length, a proximal end portion and distal end portion;
            a tapered distal end portion;
            a plurality of inflatable members positioned adjacent the distal end portion on the elongate generally rigid body;
            the plurality of inflatable members being longitudinally spaced from one another by a distance of 2 cm to less than 5 cm and being proximal to the tapered distal end portion; and
            the elongate generally rigid body having a solid tubular structure with a generally uniform diameter throughout the length thereof, and including a plurality of peripherally oriented lumens in fluid communication with the respective plurality of inflatable members and a central channel for extending a guidewire therethrough;
        ii) an introducer sheath including an open distal end portion and a proximal end portion;
        iii) wherein the dilator is slidably positioned inside of the introducer sheath such that a selected one of the plurality of inflatable members is positioned adjacent the open distal end portion of the introducer sheath;
    b) advancing the dilator-introducer sheath complex through an aneurysm in a blood vessel selected from the group consisting of a thoracic aorta, an abdominal aorta, and an iliac artery, until the open distal end portion of the introducer sheath passes the aneurysm in the associated blood vessel;
    c) withdrawing, after step b), the introducer sheath such that the selected one inflatable member passes through and is positioned on the open distal end portion of the introducer sheath;
    d) inflating, after step c), the selected one inflatable member to stop an antegrade flow of blood through the associated blood vessel; and
    e) repairing the aneurysm.

2. The method of claim 1, wherein:
the step b) comprises advancing the dilator-introducer sheath complex through an aneurysm in a thoracic aorta.

3. The method of claim 1, wherein:
the step b) comprises advancing the dilator-introducer sheath complex through an aneurysm in an abdominal aorta.

4. The method of claim 1, wherein:
the step b) comprises advancing the dilator-introducer sheath complex through an aneurysm in an iliac artery.

5. The method of claim 1, wherein:
the aneurysm includes a perforation, tear, or rupture.

6. A method of repairing an aneurysm in an arterial blood vessel of a subject, comprising the steps of:
    a) providing a dilator-introducer sheath complex, consisting of:
        i) a dilator, consisting of:
            an elongate generally rigid body having a length, a proximal end portion and distal end portion;
            a tapered distal end portion;
            a plurality of inflatable members positioned adjacent the distal end portion on the elongate generally rigid body;
            the plurality of inflatable members being longitudinally spaced from one another by a distance of 2 cm to less than 5 cm and being proximal to the tapered distal end portion; and
            the elongate generally rigid body having a solid tubular structure with a generally uniform diameter throughout the length thereof, and including a plurality of peripherally oriented lumens in fluid communication with the respective plurality of inflatable members and a central channel for extending a guidewire therethrough;
        ii) an introducer sheath including an open distal end portion and a proximal end portion;
        iii) wherein the dilator is slidably positioned inside of the introducer sheath such that a selected one of the plurality of inflatable members is positioned adjacent the open distal end portion of the introducer sheath;
    b) advancing the dilator-introducer sheath complex through an aneurysm in a blood vessel selected from the group consisting of a thoracic aorta, an abdominal aorta, and an iliac artery, until the open distal end portion of the introducer sheath passes the aneurysm in the associated blood vessel;
    c) withdrawing, after step b), the introducer sheath such that the selected one inflatable member passes through the open distal end portion of the introducer sheath;
    d) inflating, after step c), the selected one inflatable member to stop an antegrade flow of blood through the associated blood vessel;
    e) further withdrawing, after step d), the introducer sheath such that a selected second of the inflatable members passes through the open distal end portion of the introducer sheath;
    f) inflating, after step e), the selected second inflatable member to stop a retrograde flow of blood through the associated blood vessel; and
    g) repairing the aneurysm.

7. The method of claim 6, wherein:
the step b) comprises advancing the dilator-introducer sheath complex through an aneurysm in a thoracic aorta.

8. The method of claim 6, wherein:
the step b) comprises advancing the dilator-introducer sheath complex through an aneurysm in an abdominal aorta.

9. The method of claim 6, wherein:
the step b) comprises advancing the dilator-introducer sheath complex through an aneurysm in an iliac artery.

10. The method of claim 6, wherein:
the aneurysm includes a perforation, tear, or rupture.

11. A method of controlling bleeding from an arterial blood vessel of a subject, comprising the steps of:
   a) providing a dilator-introducer sheath complex, consisting of:
      i) a dilator, consisting of:
         an elongate generally rigid body having a length, a proximal end portion and distal end portion;
         a tapered distal end portion;
         a plurality of inflatable members positioned adjacent the distal end portion on the elongate generally rigid body;
         the plurality of inflatable members being longitudinally spaced from one another by a distance of 2 cm to less than 5 cm and being proximal to the tapered distal end portion; and
         the elongate generally rigid body having a solid tubular structure with a generally uniform diameter throughout the length thereof, and including a plurality of peripherally oriented lumens in fluid communication with the respective plurality of inflatable members and a central channel for extending a guidewire therethrough;
      ii) an introducer sheath including an open distal end portion and a proximal end portion;
      iii) wherein the dilator is slidably positioned inside of the introducer sheath such that a selected one of the plurality of inflatable members is positioned adjacent the open distal end portion of the introducer sheath;
   b) advancing the dilator-introducer sheath complex through a bleeding blood vessel selected from the group consisting of a thoracic aorta, an abdominal aorta, and an iliac artery, until the open distal end portion of the introducer sheath passes a bleeding point in the associated blood vessel;
   c) withdrawing, after step b), the introducer sheath such that the selected one inflatable member passes through and is positioned on the open distal end portion of the introducer sheath;
   d) inflating, after step c), the selected one inflatable member to stop an antegrade flow of blood through the associated blood vessel;
   e) repairing the bleeding blood vessel.

12. The method of claim 11, wherein:
the step b) comprises advancing the dilator-introducer sheath complex through a thoracic aorta.

13. The method of claim 11, wherein:
the step b) comprises advancing the dilator-introducer sheath complex through an abdominal aorta.

14. The method of claim 11, wherein:
the step b) comprises advancing the dilator-introducer sheath complex through an iliac artery.

15. The method of claim 11, wherein:
the bleeding point includes a perforation, tear, or rupture.

16. A method of controlling bleeding from an arterial blood vessel of a subject, comprising the steps of:
   a) providing a dilator-introducer sheath complex, consisting of:
      i) a dilator, consisting of:
         an elongate generally rigid body having a length, a proximal end portion and distal end portion;
         a tapered distal end portion;
         a plurality of inflatable members positioned adjacent the distal end portion on the elongate generally rigid body;
         the plurality of inflatable members being longitudinally spaced from one another by a distance of 2 cm to less than 5 cm and being proximal to the tapered distal end portion; and
         the elongate generally rigid body having a solid tubular structure with a generally uniform diameter throughout the length thereof, and including a plurality of peripherally oriented lumens in fluid communication with the respective plurality of inflatable members and a central channel for extending a guidewire therethrough;
      ii) an introducer sheath including an open distal end portion and a proximal end portion;
      iii) wherein the dilator is slidably positioned inside of the introducer sheath such that a selected one of the plurality of inflatable members is positioned adjacent the open distal end portion of the introducer sheath;
   b) advancing the dilator-introducer sheath complex through a bleeding blood vessel selected from the group consisting of a thoracic aorta, an abdominal aorta, and an iliac artery, until the open distal end portion of the introducer sheath passes a bleeding point in the associated blood vessel;
   c) withdrawing, after step b), the introducer sheath such that the selected one inflatable member passes through the open distal end portion of the introducer sheath;
   d) inflating, after step c), the selected one inflatable member to stop an antegrade flow of blood through the associated blood vessel;
   e) further withdrawing, after step d), the introducer sheath such that a selected second of the inflatable members passes through and is positioned on the open distal end portion of the introducer sheath;
   f) inflating, after step e), the selected second inflatable member to stop a retrograde flow of blood through the associated blood vessel; and
   g) repairing the bleeding blood vessel.

17. The method of claim 16, wherein:
the step b) comprises advancing the dilator-introducer sheath complex through in a thoracic aorta.

18. The method of claim 16, wherein:
the step b) comprises advancing the dilator-introducer sheath complex through an abdominal aorta.

19. The method of claim 16, wherein:
the step b) comprises advancing the dilator-introducer sheath complex through an iliac artery.

20. The method of claim 16, wherein:
the bleeding point includes a perforation, tear, or rupture.

* * * * *